| United States Patent [19]
Owen et al.

[11] 4,251,470
[45] Feb. 17, 1981

[54] PROCESS FOR PREPARING DI[P-(1,1,3,3-TETRAMETHYLBUTYL)PHENYL] PHOSPHORIC ACID ESTER

[75] Inventors: Jeffrey D. Owen; Harold M. Brown, both of Salt Lake City, Utah

[73] Assignee: University of Utah, Salt Lake City, Utah

[21] Appl. No.: 88,698

[22] Filed: Oct. 26, 1979

Related U.S. Application Data

[62] Division of Ser. No. 890,758, Mar. 27, 1978, abandoned.

[51] Int. Cl.³ ................................................ C07F 9/09
[52] U.S. Cl. ................................. 260/990; 204/195 M; 260/965; 260/974
[58] Field of Search ................................. 260/990, 963

[56] References Cited
U.S. PATENT DOCUMENTS 4,051,202  9/1977  Arnold, Jr. .......................... 260/990

Primary Examiner—Anton H. Sutto
Attorney, Agent, or Firm—Thorpe, North, Western & Gold

[57] ABSTRACT

An improved electroactive material for solid state, $Ca^{++}$ sensitive electrodes comprising highly purified di-[p-(1,1,3,3-tetramethylbutyl)phenyl] phosphoric acid or the corresponding calcium salt thereof.

2 Claims, 4 Drawing Figures

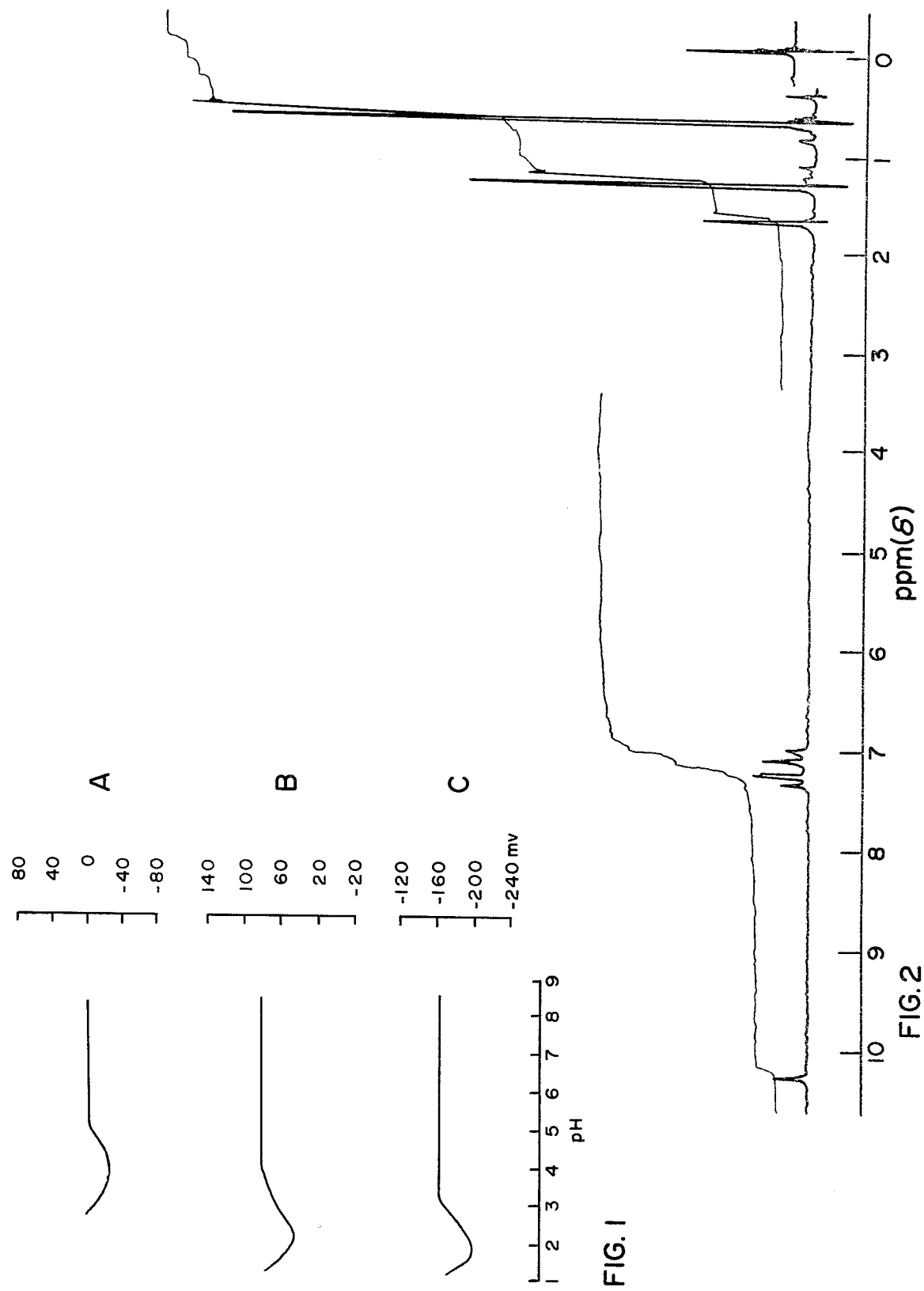

PROCESS FOR PREPARING DI[P-(1,1,3,3-TETRAMETHYLBUTYL)PHENYL] PHOSPHORIC ACID ESTER

This is a division of application Ser. No. 890,758, filed Mar. 27, 1978, now abandoned.

BACKGROUND OF THE INVENTION

1. Field of the Invention

This invention relates to $Ca^{++}$ electrode systems, and more particularly to an electrode system using a solid state electroactive membrane as $Ca^{++}$ sensitive material.

2. Prior Art

The utility of organo-phosphorus compositions in $Ca^{++}$ sensitive electrodes has long been recognized. Most prominent among such electrodes has been the Orion electrode which contains the calcium salt of didecylphosphoric acid (exchanger) dissolved in di-(n-octyl)phenylphosphonate (DOPP-n/mediator). This electrode was characterized by a response time in pure solution of about 30 seconds. Response time in impure solutions was extended as long as ten minutes.

Subsequent analysis of the Orion electrode had disclosed that at least five compounds were existent in the electroactive composition, prompting an elevation of the effects of improving purity of the exchanger-mediator combination. Griffiths, Moody and Thomas, *J. Inorg. Nucl. Chem* 34; p 3043 (1972). A similar analysis was conducted by a second research group (Ruzicka, Hansen and Tjell, *Anal. Chem Acta* 67, p 155, (1973); however, the results of both investigations demonstrated minimal improvement with use of purified components.

An attempt to improve the Orion electrode was also made by Cosgrove, et al (U.S. Pat. No. 3,729,401) utilizing the calcium salt of di-[p-(1,1,3,3,-tetramethybutyl)-phenyl] phosphoric acid (herein referred to as t-HDOPP.) The compound, whose physical state was described as "normally" solid, was dissolved in an organic phase and used without mediators. No concern is reflected by this disclosure as to method of preparation or purity of the t-HDOPP constituent. The fact that the composition was described as "normally" solid suggests that extreme purity was not considered to be a critical factor.

In U.S. Pat. No. 3,932,233, Ruzicka incorporates t-HDOPP into a solid state electrode having di(alkyl-)arylphosphonate as the mediator, the combination being fixed in a polyvinylchloride matrix to form a $Ca^{++}$ sensitive membrane. The amount of mediator used was 5 to 50 times the amount of exchanger, with a comparable large amount of polyvinyl chloride.

The use of this solid state, organo-phosphorus composition having predominant mediator/PVC concentration produced improvements in selectivity over $Na^+$ of a factor of $10^2$ and an improved detection limit approximately 20 times lower than previous electrodes. It has been reported, however, that these electrodes have time responses of 5-15 minutes when one day old, time responses of one minute for up to seven weeks, and are non-functional thereafter. Christoffersen and Johansen, *Anal Chem Acta* 81, p 191 (1976).

Although the preparation procedures for a di(aryl)-phosphate were outlined by Ruzicka (U.S. Pat. No. 3,932,233) the purification step did not suggest any special methods or need for extreme purification of the di(aryl)phosphate exchanger. The extraction procedure disclosed by Ruzicka clearly indicates that normal purity was intended. Neither was any experimental data recited to suggest the need for special attention to the purification step.

Still another attempt to improve the Orion electrode was made by H. M. Brown, J. P. Pemberton and J. D. Owen as disclosed in *Anal Chem Acta* 85 pp 261-276 (1976). This electrode used the same electroactive material (t-HDOPP) as used previously by Cosgrove and Mask, but used the mediator (DOPP-n) of Ruzicka et al and Ross and the PVC matrix of Griffiths, et al. Although a unique procedure of using a lower percent of PVC was discovered to yield the best results in a microelectrode, conventional purity for t-HDOPP was considered adequate. Nothing had been disclosed by previous investigators to indicate the need for special attention to exchanger purity. Previous analyses of improved purity had not rendered any substantial improvement and the low concentration of exchanger in mediator and PVC would seem to suggest that efforts to use a highly purified exchanger would have little effect in view of the dilution of the t-HDOPP in a predominant mediator/PVC environment. This review of the prior art development of organophosphorus exchanger materials in $Ca^{++}$ sensitive electrodes reveals a clear conception among those most skilled in the art, that an extreme high level of exchanger purity was not considered to be a critical factor in improving electrode operation. Instead, each successive increment of progress in enhancing sensitivity and sensitivity was attributed to variation in types of exchanger material, use of mediators, improved balance in relative concentrations of solid state constituents and engineering design of the electrode apparatus. The problems of response time and stability, however, continue to present difficulty in obtaining an operable $Ca^{++}$ electrode system.

OBJECTS AND SUMMARY OF THE INVENTION

It is an object of the subject invention to provide a $Ca^{++}$ electrode with improved response time, shelf life and stability.

It is a further object of the present invention to show that utilization of a highly purified form of t-HDOPP or its corresponding clacium salt provides dramatic improvement in the shelf life and time response of $Ca^{++}$ electrode.

An additional object of this invention is to provide a method of preparation for highly purified t-HDOPP.

The discovery that t-HDOPP and its related calcium salt provide unique and unexpected improvement in $Ca^{++}$ electrode efficiency by greatly reducing response time and increasing electrode shelf life is particularly significant to $Ca^{++}$ electrode technology. It has now been shown that utilization of t-HDOPP which is at least 96 percent pure, reduces time response in obtaining a stable measurement from several minutes to several seconds. These results have been specifically demonstrated in a solid state mediator/PVC/t-HDOPP membrane in a $Ca^{++}$ electrode.

Other objects and features will be obvious to persons skilled in the art from the following detailed description, taken with the accompanying drawings, in which:

FIG. 1 presents a graphic comparison of the characteristic pH drop associated with organo-phosphate exchange materials.

FIG. 2 shows an NMR spectra on the subject compound.

FIG. 3 graphically illustrates alkalimetric titration data regarding the subject compound.

FIG. 4 shows the improved time response of the subject invention.

DETAILED DESCRIPTION OF THE INVENTION

Figure 3:
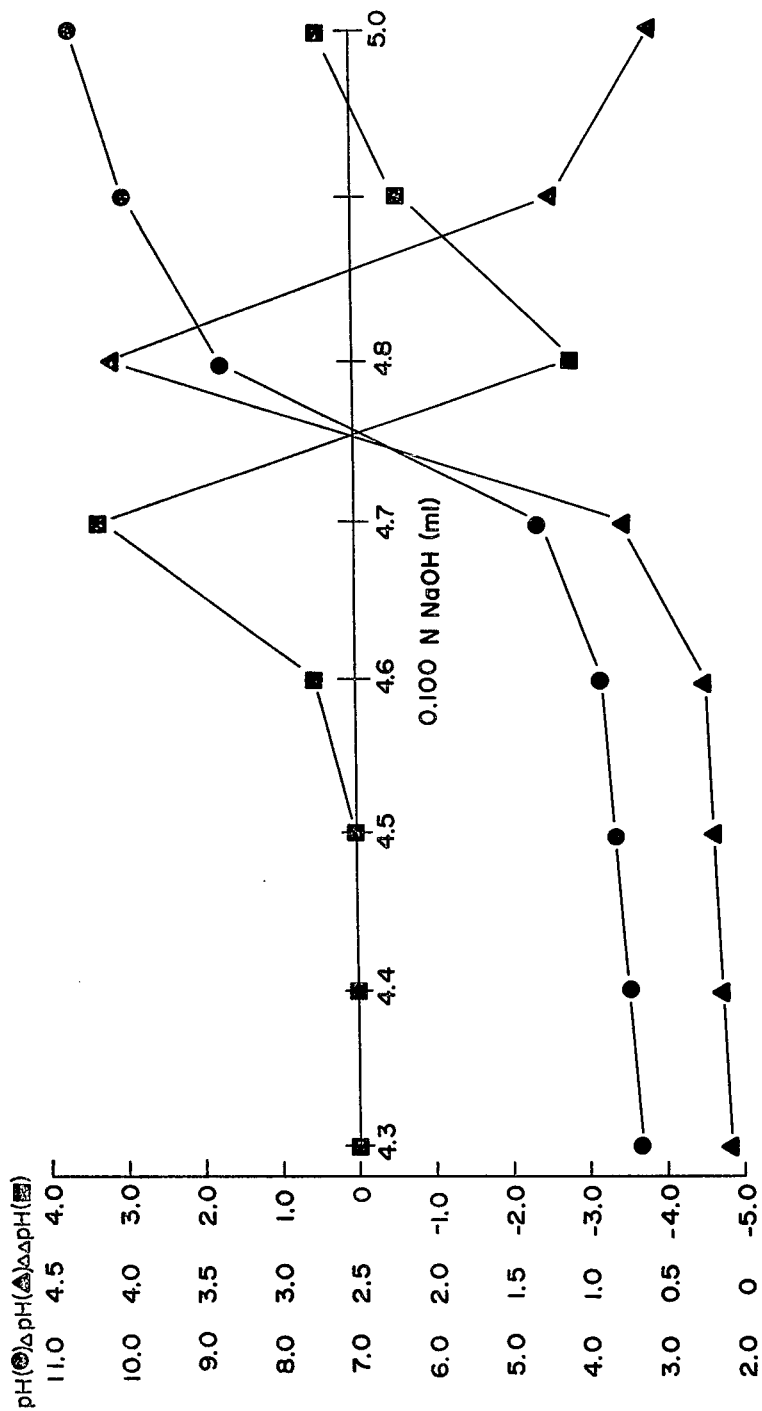

The present invention incorporates the use of t-HDOPP or its corresponding calcium salt as exchange material in a $Ca^{++}$ electrode. When the exchange material is approximately 96 percent pure or better, the electrode develops surprising stability and short time response.

Whereas previous $Ca^{++}$ electrodes using t-HDOPP have required up to several minutes to provide a steady-state measure of calcium ion concentration, the electrode using a t-HDOPP material of at least 96 percent purity, requires only 1–2 seconds to reach a stabilized reading. Although the explanation is not totally understood, it now appears that removal of substantially all of the mono-ester from the t-HDOPP diester enables the latter to transfer $Ca^{++}$ within the membrane at a surprisingly much faster rate.

In addition to the improved response of the electrode, pure t-HDOPP adds unexpected shelf life. As has been stated, previous $Ca^{++}$ electrodes using a di(aryl)phosphate have not been operable after approximately seven weeks. The use of t-HDOPP which is at least 96 percent pure has demonstrated utility well past two month periods. This has been experimentally confirmed by microelectrodes having a t-HDOPP constituent of 99 percent purity which have operated effectively after two months.

Finally, the eratic variations of time response exhibited by Christophersen, supra, are not experienced when using highly purified electroactive material. Accurate electrode response is not only immediate, but the nature of response remains substantially constant over the life of the electrode.

A comparison of characteristics of the improved $Ca^{++}$ electrode of the present invention (C) with the Orion (A) and Ruzicka (B) electrodes is illustrated in FIG. 1. All test solutions were at a $Ca^{++}$ concentration of $10^{-3}$ M. Referring to this comparison, the improved performance of the present invention is illustrated in the characteristic dip for pH interference from pH 4.5 to pH 3.5 for the present invention.

The interference caused by this characteristic pH dip common to organo-phosphate exchange materials is further exaggerated when the $Ca^{++}$ concentration being measured is very low. With decreasing $Ca^{++}$ concentration, the pH interference becomes more predominant and the size of the dip increases. Consequently, prior to the present invention effective $Ca^{++}$ concentration measurements at very low pH values were impossible. By utilizing highly purified t-HDOPP, however, the resulting increased sensitivity permits successful detection of low $Ca^{++}$ in low pH environments.

With respect to preparation of highly purified t-HDOPP, the present inventors encountered significant difficulty in utilizing the synthesis procedures outlined in the previously cited references or other references currently available. As a consequence, a new method of preparation was developed which yielded a t-HDOPP product of 99 percent purity or better. This method comprises the following steps; which appear to act synergistically in combination:

Step 1. 2.5 moles of tert-octyl phenol and 2.5 moles of pyridine were dissolved in 85 percent petroleum ether (60°–90° BP)/15% diethyl ether (500 ml) and placed in a round-bottomed flask with a reflux adapter. One mole of phosphorus oxytrichloride ($POCl_3$) was dissolved in an equal volume of the previous ether mixture solvent and was added slowly to the previous solution. The resulting white mixture was stirred for 15–30 minutes.

Step 2. The white floculant precipitate of the step was separated from the mixture by filtering several times through a Bunchner funnel with Whatman #1 filter paper. To remove the remainder of trace pyridine-hydrochloride, a millipore filter with $0.3\mu$ pores was utilized.

Step 3. A remaining sauterne-colored clear oily liquid from Step 2 was next evaporated to a thick oily liquid by using a rotoevaporator with a vacuum at room temperature.

Step 4. The product from Step 3 was poured into a beaker and 2 moles of NaOH added. The mixture was stirred continuously upon addition of the NaOH.

Step 5. Diethyl ester (500 ml) was then added to the contents of Step 4 beaker, stirring continued for ten minutes. The organic ether phase (top layer) was extracted and the bottom organic phase was discarded using a separatory funnel.

Step 6. The organic phase from Step 5 was then placed in a large flask. Water (1 liter) and about 0.1 mole of NaOH were added, stirring continuously. An aqueous solution containing 1 mole of $BaCl_2.2H_2O$ was then added to the resulting mixture, forming a white precipitate in less than five minutes.

Step 7. The precipitate from Step 6 was filtered in a Buchner funnel and washed several times with benzene.

Step 8. The precipitate from Step 7 was dissolved in petroleum ether (500 ml) in a large beaker. Approximately an equal volume of 1 N HCl was added and the mixture stirred for one hour. The top organic phase was then separated and washed with 1 N HCl in a separatory funnel until no white $BaSO_4$ formed upon adding $H_2SO_4$ to the discarded bottom aqueous layer.

Step 9. The solvent was rotoevaporated at room temperature under vacuum, leaving a white product.

Step 10. the product of Step 9 was next dissolved in benzene (500 ml) and washed with ethylene glycol several times in a separatory funnel. The lower layer of ethylene glycol washes was discarded.

Step 11. The benzene layer was then washed with 1 M HCl several times in a separatory funnel and dryed over anhydrous $Na_2SO_4$.

Step 12. The final product of t-HDOPP was obtained by rotoevaporating off the solvent in the previous step. Alternatively, the product can be recrystallized out of a solution of cold acetone, ethanol or diethyl ether, after the volume of solvent in Step 11 is first reduced, a 20 percent yield is obtained.

The melting point for the compound is 95°–97° C. It should be noted that this value is higher than values previously reported in Cattrall, R. W. and Drew, D. M., *Anal. Chem Acta* 76: 269–277 (1975), suggesting improved purity. The compound is also always white, as opposed to previous descriptions which suggested otherwise.

Elemental analysis was performed by Galbraith Laboratories, Inc., and was found to be as follows:

| Element | Experimental | Theoretical for t-HDOPP | % Mean Relative Error |
|---------|--------------|------------------------|----------------------|
| C | 70.29 ± 0.20* | 70.89% | 0.85 |
| H | 9.03 ± 0.18* | 9.07% | 0.44 |
| P | 6.79 ± 0.14* | 6.54% | 3.82 |

*Mean value ± Standard Deviation for analysis of three separate synthesis products.

No discrepancy between the experimental and theoretical is less than 1 percent for carbon and hydrogen analysis. It is somewhat higher for phosphorous (3.82%), probably indicating the increased difficulty of this test as compared with the routine analysis for carbon and hydrogen. Also, this is probably within the error of their experimental procedure since it has such a low percentage in t-HDOPP.

FIG. 2 shows the NMR trace for the product and integration in the upper portion of the figure. The peak at about 10.3 ppm denotes the hydrogen of the single —OH group; the four peaks at 7.4 to 7.0 ppm represent the four aromatic hydrogens, the peak at 1.7 ppm is for the two hydrogens on the $CH_2$ group; the peak at 1.3 ppm is for the six hydrogens on the two $CH_3$ groups on the carbon closest to the phenyl group and large peak at 0.7 ppm is for the nine hydrogens on the three $CH_3$ groups on the third carbon from the phenyl group.

The NMR analysis indicates the presence of a very pure organic acidic compound. This is noted by the absence of "stray" peaks which do not conform to the structure of pure t-HDOPP. The ratio of $CH_2$, $CH_3$, phenyl, and acid protons can be measured by taking the height of the integration curve, as shown over the respective NMR peaks. This indicates the molecule has the same set of ratios of different hydrogen protons as t-HDOPP.

These hydrogen protons are more clearly represented by the following structure for t-HDOPP:

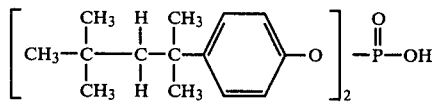

This structure and purity is further confirmed by the alkalimetric titration of t-HDOPP for the determination of molecular weight, reflected in FIG. 3. The end point of the titration as shown in the Figure is denoted by the intersection at zero of the second derivative of the pH, or $\Delta\Delta pH$, at 4.75 ml of 0.100 n NaOH. This corresponds to $4.75 \times 10^{-4}$ equivalents of base needed to neutralize 0.2264 g of t-HDOPP. Since t-HDOPP has a single acid group, this also represents the amount of equivalents of acid present. The molecular weight, therefore is $(0.2264 \text{ g}/4.75 \times 10^{-3} \text{ eq})$ 476.6–477. This is a relative error of less than 1% over the theoretical value of 474 for 100 percent pure t-HDOPP.

Figure 4:
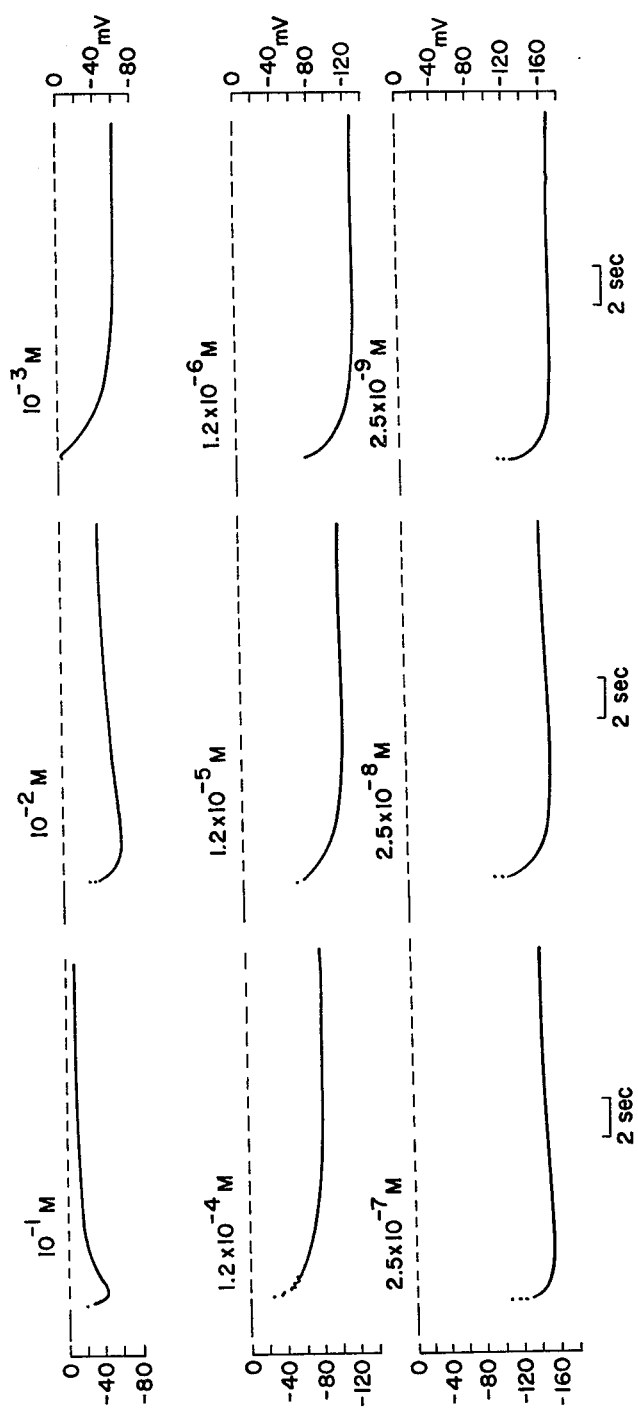

Utilization of this substantially pure t-HDOPP or corresponding calcium salt not only gives the improved detection capability as illustrated in FIG. 1, but also develops a profound improvement in time response of an electrode upon insertion in a test solution. The time responses for a 1 micrometer tip microelectrode are shown in FIG. 4, representing $Ca^{++}$ concentrations ranging from $10^{-1}$ M to $2.5 \times 10^{-9}$ M. It should be noted that all steady state conditions were reached within 10 seconds from insertion, and many responses were less than five seconds. These responses, therefore, represent at least a ten fold improvement over the prior art: in addition to providing the increased stability as previously discussed.

Although preferred forms of the invention have been herein described, it is to be understood that the present disclosure is by way of example and that variations are possible without departing from the scope of the hereinafter claimed subject matter, which subject matter is to be regarded as the invention.

We claim:

1. A method for preparing di [p-(1,1,3,3-tetramethylbutyl) phenyl] phosphoric acid having at least 96 percent purity comprising the following steps, utilizing reactant quantities having relative proportions substantially equal to those stated herein, the method comprising:

a. dissolving 2.5 moles of tert-octyl phenol and 2.5 moles of pyridine mixture of petroleum ether/diethyl ether (approximately 95%/15% respectively);
   b. dissolving 1 mole of phosphorus oxytrichloride in a mixture of petroleum ether-diethyl ether (approximately 85%/15% respectively);
   c. adding the solution of step "b" to the solution of step "a", while refluxing the combination, and stirring the resulting white mixture for 15–30 minutes;
   d. separating the white flocculant precipitate of the mixture of the previous step with filter means equivalent to $0.3\mu$ pore capability;
   e. evaporating the remaining sauterine-colored clear oily liquid of the previous step to a thick oily liquid;
   f. adding approximately 2 moles of NaOH and diluting with diethyl ether while stirring continuously for approximately ten minutes;
   g. extracting the organic ether phase (top layer) of the previous mixture for use with the following steps;
   h. adding water and approximately 0.1 mole of NaOH to the previous organic phase, while stirring continuously;
   i. adding an aqueous solution of 1 mole $BaCl_2 \cdot 2H_2O$ to the mixture of the previous step, forming a white precipitate;
   j. filtering the white precipitate of step i and washing the same with benzene;
   k. dissolving the washed precipitate in pretroleum ether;
   l. adding a volume of 1 N HCl substantially equal to the volume of the previous step, to the dissolved precipitate and stirring for about an hour;
   m. separating the organic phase of the mixture of step l (top layer) and washing the same with 1 N HCl until no white $BaSO_4$ is formed upon addition of $H_2SO_4$ to the bottom aqueous phase;
   n. evaporating the organic phase to form a white product;
   o. dissolving this product in benzene and washing with ethylene glycol in a separatory funnel;
   p. washing the benzene layer with 1 N HCl in a separatory funnel and drying over anhydrous $Na_2SO_4$;
   q. removing the benzene solvent to isolate the final product.

2. A method as defined in claim 1, wherein the removal step "q" is selected from the group of steps consisting of (a) evaporating the solvent of step "q", and (b) recrystalizing the product out of a solution of cold solvents selected from the group consisting of acetone, ethanol and diethyl ether.